(12) United States Patent  
Prinzhausen et al.

(10) Patent No.: US 6,943,895 B2
(45) Date of Patent: Sep. 13, 2005

(54) INTERFEROMETRIC MEASURING DEVICE

(75) Inventors: Friedrich Prinzhausen, Stuttgart (DE); Michael Lindner, Leutenbach (DE)

(73) Assignee: Robert Bosch GmbH, Stuttgart (DE)

( * ) Notice: Subject to any disclaimer, the term of this patent is extended or adjusted under 35 U.S.C. 154(b) by 167 days.

(21) Appl. No.: 10/221,294
(22) PCT Filed: Mar. 29, 2001
(86) PCT No.: PCT/DE01/01191
§ 371 (c)(1), (2), (4) Date: Sep. 10, 2002
(87) PCT Pub. No.: WO01/75395
PCT Pub. Date: Oct. 11, 2001

(65) Prior Publication Data
US 2003/0048454 A1 Mar. 13, 2003

(30) Foreign Application Priority Data

| Mar. 30, 2000 | (DE) | .......................................... 100 15 878 |
| Dec. 23, 2000 | (DE) | .......................................... 100 65 179 |
| Mar. 28, 2001 | (DE) | .......................................... 101 15 524 |

(51) Int. Cl.⁷ .............................................. G01B 9/02
(52) U.S. Cl. ....................................... 356/497; 356/511
(58) Field of Search ................................ 356/479, 487, 356/511, 512, 513, 514, 497

(56) References Cited

U.S. PATENT DOCUMENTS

| 5,877,856 A | 3/1999 | Fercher |
| 6,144,449 A | 11/2000 | Knuettek et ak. |
| 6,822,746 B2 * | 11/2004 | Prinzhausen et al. ....... 356/497 |

FOREIGN PATENT DOCUMENTS

| DE | 91 01 682.7 | 7/1991 |
| DE | 41 08 944 A1 | 9/1992 |
| DE | 197 04 602 | 8/1998 |
| DE | 100 47 495 A1 | 10/2001 |
| WO | 97 27468 A | 7/1997 |
| WO | 97 32182 A | 9/1997 |
| WO | 99 46557 A | 9/1999 |

OTHER PUBLICATIONS

Peter De Grott., et al: "Surface Profiling by Analysis of White–Light Interferograms . . . " J. Mod Opt., vol. 42, No. 2, 389–401, 1995.

T. Maack et al: "Endoskopisches 3–D–Formmesssystem", in Jahrbuch Fier Optik und Feinmechanik, Ed. W.–D. Prenzel, Verlag Schiele und Schoen, Berlin, 231–240, 1998.

* cited by examiner

Primary Examiner—Andrew H. Lee
(74) Attorney, Agent, or Firm—Michael J. Striker

(57) ABSTRACT

The interferometric measuring device (1) for measuring the shape of a surface of an object (O) has a radiation source (LQ), a beam splitter (ST) producing an object beam (OS) guided along an object light path to the object (O) and a reference beam (RS) guided along a reference light path to a reflective reference plane (RSP), an image recorder (BA) that records interfering radiation reflected by the object (O) and the reference plane (RSP) and an associated evaluation device (E) to determine the surface shape. A favorable adaptability and operation are achieved by arrangement of a fixed lens system (SO) that produces a fixed intermediate image (SZB) in the object light path and a movable lens system (BO) that is movable in a direction of its optical axis for depth scanning. The image recorder (BA) has pixels arranged next to each other on an extended planar surface.

24 Claims, 14 Drawing Sheets

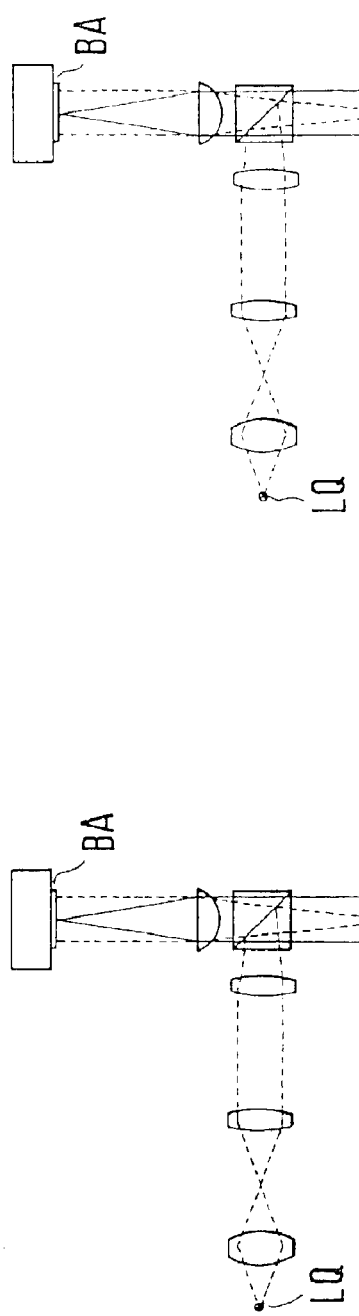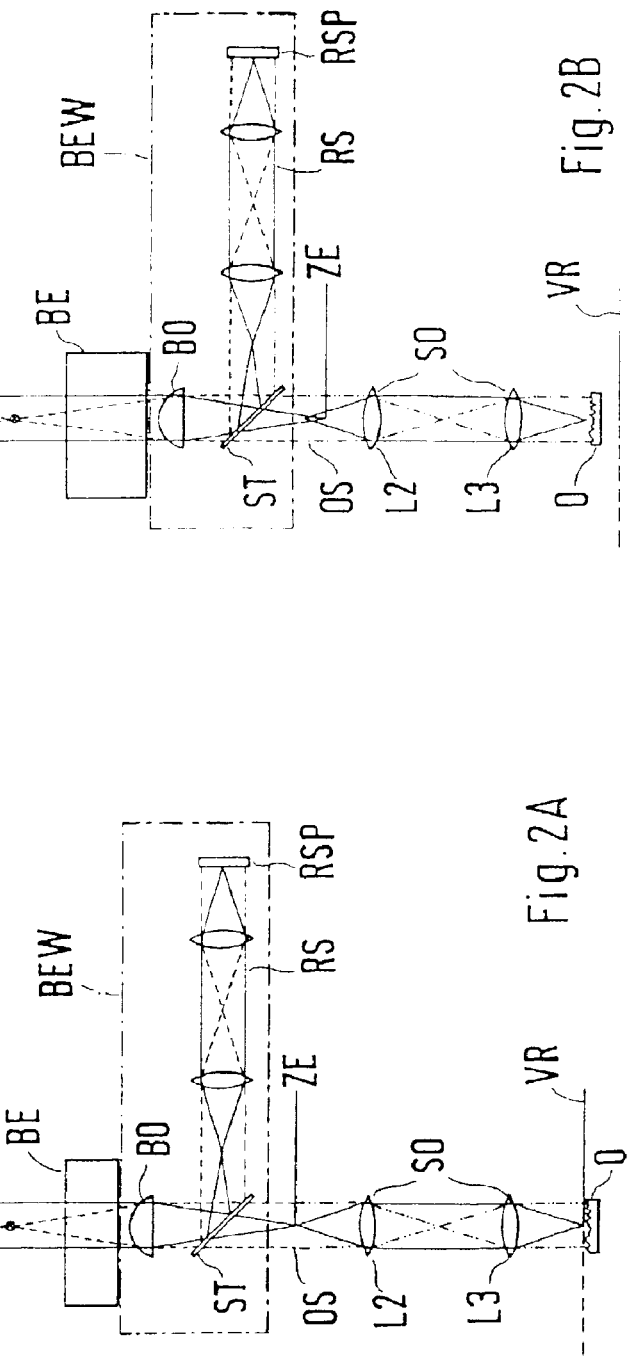
Fig. 2A
Fig. 2B

INTERFEROMETRIC MEASURING DEVICE

BACKGROUND OF THE INVENTION

The invention is based on an interferometric measuring device for measuring the shape of a surface of an object, with a radiation source that emits a short coherence radiation, a beam splitter for producing an object beam, which is guided along an object light path to the object, and a reference beam, which is guided along a reference light path to a reflective reference plane, and with an image recorder that records the radiation, which is reflected by the object and the reference plane and is brought into interference, and supplies it to an evaluation device to determine the surface shape.

An interferometric measuring device of this kind has been disclosed by DE 41 08 944 A1. In this known interferometric measuring device, which is based on the measuring principle of so-called white light interferometry or short coherence interferometry, a radiation source emits short coherence radiation, which a beam splitter splits into an object beam that illuminates a measurement object and a reference beam that illuminates a reflective reference plane in the form of a reference mirror. In order to scan the object surface in the depth direction, the reference mirror is moved in the direction of the optical axis of the reference light path by means of a piezoelectric actuating element. When the object light path and the reference light path coincide, then in the range of the coherence length, there is a maximum of interference contrast, which can be detected by means of a photoelectric image recorder and a subsequent evaluation device and is evaluated on the basis of the known deflection position of the reference mirror in order to determine the contour of the object surface.

Other interferometric measuring devices or interferometric measuring methods of this kind based on white light interferometry are given in "Surface Profiling by Analysis of White-Light Interferograms in the Spatial Frequency Domain" by P. de Groot and L. Deck, in the *Journal of Modern Optics*, Vol. 42, No. 2, pp. 389–401, 1995 and in "Endoskopisches 3-D-Formmesssytem" [Endoscopic 3-D Shape-Measuring System] by T. Maack, G. Notni, W. Schreiber, and W.-D. Prenzel, in the *Jahrbuch für Optik und Feinmechanik* [Annual of Optics and Fine Mechanics], Ed. W.-D. Prenzel, Verlag Schiele und Schoen, Berlin, pp. 231–240, 1998.

With the above-mentioned interferometric measuring devices and measuring methods, it is difficult to execute measurements of different locations, in particular ones that are difficult to access, e.g. in deep cavities or narrow channels, with a sufficient degree of lateral resolution. In order to eliminate this problem, the (unpublished) German Patent Application No. 199 48 813 proposes generating at least one intermediate image in the arm of the object light path, which achieves a greater lateral resolution even in a narrow cavity or narrow channel. On the other hand, enlarging the numerical aperture shortens the depth of focus and also, a scanning of a surface region whose normal (viewing direction) is oblique to the axis of the image-generating device of the object light path causes problems in the scanning in the depth direction.

The problem of maintaining the depth of focus range in depth scanning can be avoided in that instead of moving the reference plane or the reference mirror that represents it, the reference light path is kept fixed and the object light path is changed. This can once again take place in two different ways, i.e. on the one hand, by moving the object itself in the depth direction or on the other hand, by moving the interferometric part of the measuring device in relation to the object. These kinds of changes to the object light path as steps taken for depth scanning in white light interferometry are in fact known in and of themselves, for example from the above-mentioned journal articles, but are technically difficult to achieve, particularly in the manufacture of their parts.

SUMMARY OF THE INVENTION

The object of the invention is to produce an interferometric measuring device of the type mentioned at the beginning, which permits a simple adaptability to different measuring problems and which facilitates the achievement of the best possible measurement result with the simplest possible design and the simplest possible measurement execution.

According to the invention the interferometric measuring device for measuring the shape of an object surface comprises a radiation source that emits short coherence radiation, a beam splitter arranged to cooperate with the radiation source to produce an object beam, which is guided along an object light path to the object, and a reference beam, which is guided along a reference light path to a reflective reference plane, a fixed lens system arranged in the object light path and having a fixed relationship to the object, in order to reflect the object beam;

a movable lens system having an optical axis and following the fixed lens system, which is movable in a direction of said optical axis;

an image recorder arranged to record radiation reflected by the object and radiation reflected by the reflective reference plane with image recording elements disposed over an extended surface area thereof, the radiation reflected by the object and the reflective reference plane being arranged to interfere with each other; and an evaluation device connected with the image recorder to determine the surface shape from the interfering radiation received by the image recorder.

It is especially advantageous that the interferometric measuring device according to the invention has a fixed lens system, which is fixed in relation to the object (during measurement), is disposed in the object light path and a following movable lens system in the object light path that can move in the direction of its optical axis (during measurement).

With the fixed lens system and the movable lens system disposed after it, there are numerous possibilities to simply measure different surfaces, even in locations that are difficult to access. For example a surface aligned oblique to the movement direction of the depth scanning can be scanned in a positionally accurate manner in the depth direction by means of a deflecting element. With different image-generating elements that deform the wave front, such as refractive, diffractive, or reflective elements (e.g. lenses, concave mirrors, gratings, etc.) or a combination of optical elements of this kind, there are a variety possibilities for adapting to a respective measurement problem without requiring a costly modification to the overall design of the measuring device.

If the fixed lens system is entirely or partially embodied as an endoscope, then it is possible to achieve a relatively high lateral resolution even when measuring in narrow cavities.

If the fixed lens system is part of a lens system that generates an intermediate image, then the cost of adapting the measuring device to different measuring tasks is reduced considerably further. In this connection, it is particularly good if the intermediate image of the lens system generating in the intermediate image is disposed in the object light path.

In order to achieve a measurement that stands up to lateral relative motion of the object, the invention advantageously provides that the fixed lens system generates an image of the object toward infinity.

A variety of designs are comprised in that the movable lens system is disposed entirely outside, partially inside and outside, or entirely inside the object light path.

The measure of comprising the movable lens system entirely or partially of optic elements, which can move in the optical axis, can easily be used to produce a zoom lens, for example.

The precision of the measurement is increased by the step of placing an image of the reference plane in the depth of focus range of the lens system that generates the image of the object on the image recorder (image-generating lens system). In this connection, the image of the reference plane is advantageously placed in the image plane of the image-generating lens system and in addition, the image of the reference plane moves synchronously with the image plane of the image-generating lens system when the movable lens system moves.

An advantageous embodiment of the invention is also comprised in that the fixed lens system is embodied as a fixed intermediate image-generating device, with which at least one intermediate image of the object surface—preferably in the object light path—is generated, which is fixed in relation to the object, and that the movable lens system is embodied as an objective lens system, which is disposed behind the fixed intermediate image in the beam path and can move in the direction of its optical axis in order to scan the fixed intermediate image, which is aligned normal to this axis, in the depth direction and to generate an image of it on the image recorder directly or by means of one or more intermediate images. Generating the fixed intermediate image of the object surface, which is disposed for example in the object light path, by means of the fixed intermediate image-generating device in the object light path on the one hand makes it possible, even in narrow channels or bores, to detect the object surface to be measured with a relatively high degree of lateral resolution and makes it possible to evaluate it with regard to the depth structure through the use of the image recorder and the subsequent evaluation device. The scanning of the fixed intermediate image can be executed with relatively simple steps since only a few optical components of the object light path have to be moved to scan its depth; the scanned depth of the fixed intermediate image always remains in the depth of focus range of the movable objective lens system since by means of the depth scan, the object plane of the movable objective lens system is moved, so to speak, through the fixed intermediate image and in this manner, the interference maxima in the range of the greatest focus are evaluated. Furthermore, the fixed intermediate image is always aligned or can always be aligned normal to the movement direction of the objective lens system since even when the object surface being considered is disposed oblique relative to the axis of the object light path, an image of it can easily be generated normal to the axis of the moving objective lens system. This permits an easy measurement of surface regions whose normals are aligned oblique to the movement direction of the objective lens system.

The image generation quality and precision of the evaluation are improved by virtue of the fact that the intermediate image-generating device has the same image-generating scale for all of the object points that appear in the intermediate image. For example, the design can be embodied in such a way that the intermediate image-generating device is embodied as a telecentric image-generating device in a 4f apparatus.

In order to achieve more precise measuring results, it is also advantageous that a lens system, which at least partially corresponds to (or is identical to) the lens system in the object light path, is provided in the reference light path for compensation.

An advantageous embodiment of the measuring device for executing a large-area evaluation of the surface region being considered is comprised in that the image recorder has image recording elements (pixels) disposed over a large area and that for each pixel, the position of the objective lens system at which the greatest interference contrast occurs is detected.

The depth scanning of an obliquely disposed object surface is easily permitted by virtue of the fact that when a viewing direction of the intermediate image-generating device diverges from the normal of the object surface, an image-generating unit is provided for generating the intermediate image.

A simple, easy-to-use design of the measuring device is improved by virtue of the fact that a movable unit includes an illumination unit with the light source and the beam splitter in addition to the movable objective lens system or includes only the beam splitter in addition to the movable objective lens system.

An embodiment of the measuring device that is favorable from both an operational and a design standpoint is also comprised in that the fixed intermediate image-generating device is embodied as an endoscope.

The measure of providing a set of fiber optics to illuminate the object and the reference plane achieves the advantage that reflections against the lenses of the image-generating device are reduced.

Various possible embodiments of the light paths are achieved by virtue of the fact that the lenses of the object light path, the reference light path, and other light paths are achromatic lenses, grin lenses (gradient index lenses), or rod-shaped lenses.

The shape measurement is improved by virtue of the fact that an optical element is disposed in the image-generating lens system, inside or outside the object light path, which permits the image to be rotated into a position that is favorable for the evaluation.

Access to a measuring location inside an object can be facilitated by virtue of the fact that a tilting endoscope, as the fixed lens system or part of the fixed lens system, is disposed in the object light path and can be moved into at least two tilt positions with an angle between the untilted and tilted positions.

The invention advantageously provides that the tilting endoscope has two tubes, which are connected to each other by means of a joint and which contain optical components of the tilting endoscope including a deflecting element.

The tilt positions can be easily set by virtue of the fact that a spring mechanism is provided in the vicinity of the joint and cooperates with the two tubes.

BRIEF DESCRIPTION OF THE SEVERAL VIEWS OF THE DRAWING

The invention will be explained in detail below in conjunction with exemplary embodiments with reference to the drawings.

FIGS. 2A and 2B show depictions of another exemplary embodiment of the interferometric measuring device, where the deflecting element is replaced by image-generating elements that deform the wave front, in two different scanning positions.

DETAILED DESCRIPTION OF THE INVENTION

Figure 1A:
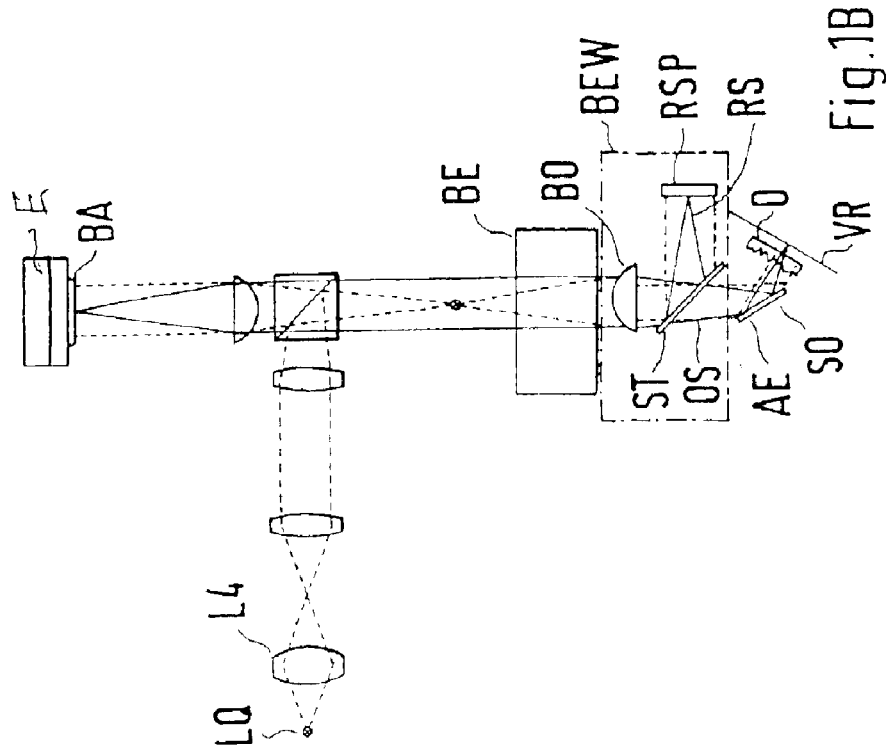
FIGS. 1A and 1B show schematic depictions of a first exemplary embodiment of an interferometric measuring device, with a deflecting unit that is fixed in relation to an object, in two different depth scanning positions.
Figure 1B:
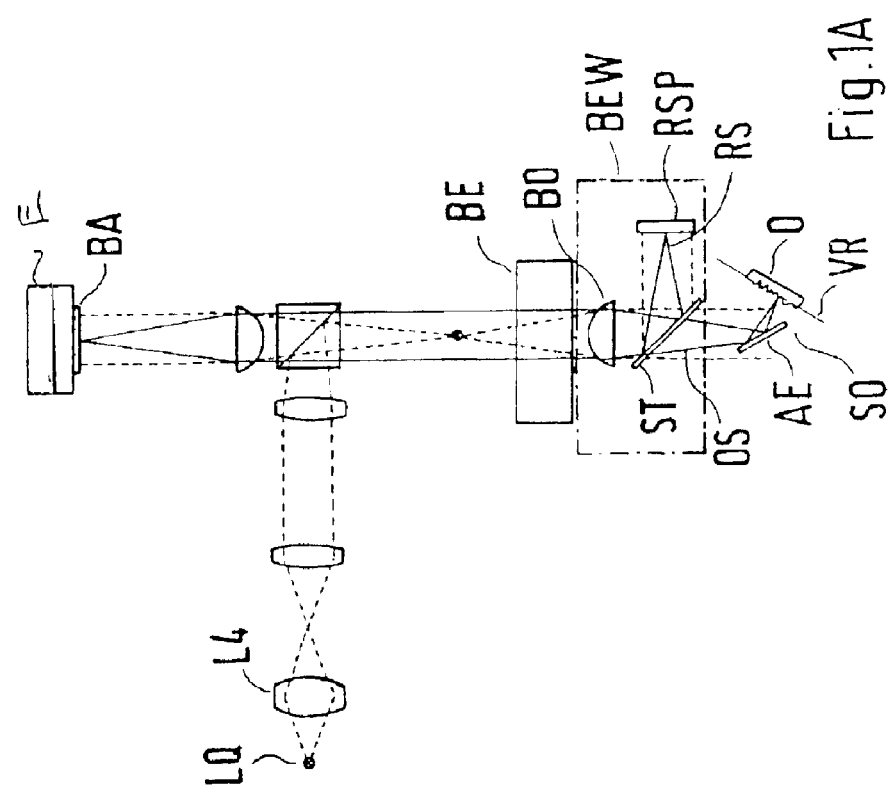

In an interferometric measuring device 1 shown in FIGS. 1A and 1B, short coherence radiation of a radiation source or light source LQ (e.g. a light-emitting diode or superluminescence diode) whose coherence length is typically on an order of magnitude of approx. 10 $\mu$m (e.g. 3 to 100 $\mu$m) is conveyed via a lens L4 and other optical elements to a beam splitter ST and is split in this beam splitter ST into an object beam OS, which is guided to a surface of an object O, and a reference beam RS, which is guided to a reference mirror RSP.

In the object light path or object arm, a fixed lens system SO in the form of a reflective deflecting unit AE is disposed in front of the object O so that the obliquely positioned object O is always scanned perpendicular to its surface in the depth direction, as shown in FIGS. 1A and 1B, in which two different scanning depths are shown, which are produced by deflecting a moving unit BEW by means of a movement generator BE attached to it, for example a piezoelectric element. A virtual reference plane VR is therefore situated in the normal direction at various depths in relation to the object O. The fixed lens system SO, which in this instance is constituted by the deflecting unit AE, is fixed in relation to the object O. It is followed in the beam path by a movable lens system BO, which is disposed in the moving unit BEW, in the beam path between the beam splitter ST and the image recorder A.

During the depth scanning, if the object light path and the reference light path coincide due to the movement of the moving unit BEW, then a maximum of the interference contrast is produced in the range of the coherence length, which interference contrast is detected by means of the photoelectric image recorder BA and a subsequent evaluation device and is evaluated based on the known deflection position in order to determine the contour of the object surface.

In the additional exemplary embodiment shown in FIGS. 2A and 2B, in which two different deflection positions of the moving unit BEW produced by the movement generator BE are shown, in comparison to the previous exemplary embodiment, the fixed lens system SO is embodied differently, namely by means of image-generating elements in the form of lenses L2, L3 that deform the wave front. The fixed lens system SO generates a fixed intermediate image in an intermediate image plane ZE, which is scanned in the depth direction by means of the movable lens system disposed in the moving unit BEW. This measure makes it possible to simply adapt essentially the same scanning unit to different measuring situations; for example, a measurement with a relatively high degree of lateral resolution in narrow cavities is achieved. There is also no trouble with regard to depth of focus since the object surface is always optimally aligned in relation to the image-generating movable lens system BO. By means of the image-generating lens system, which contains the fixed lens system SO and the movable lens system BO, an image of the object O is generated on the image recorder BA. Through the appropriate arrangement of the components in the moving unit BEW, it is possible to move the image of the reference plane VR along with the image plane of the image-generating lens system.

Figure 3:
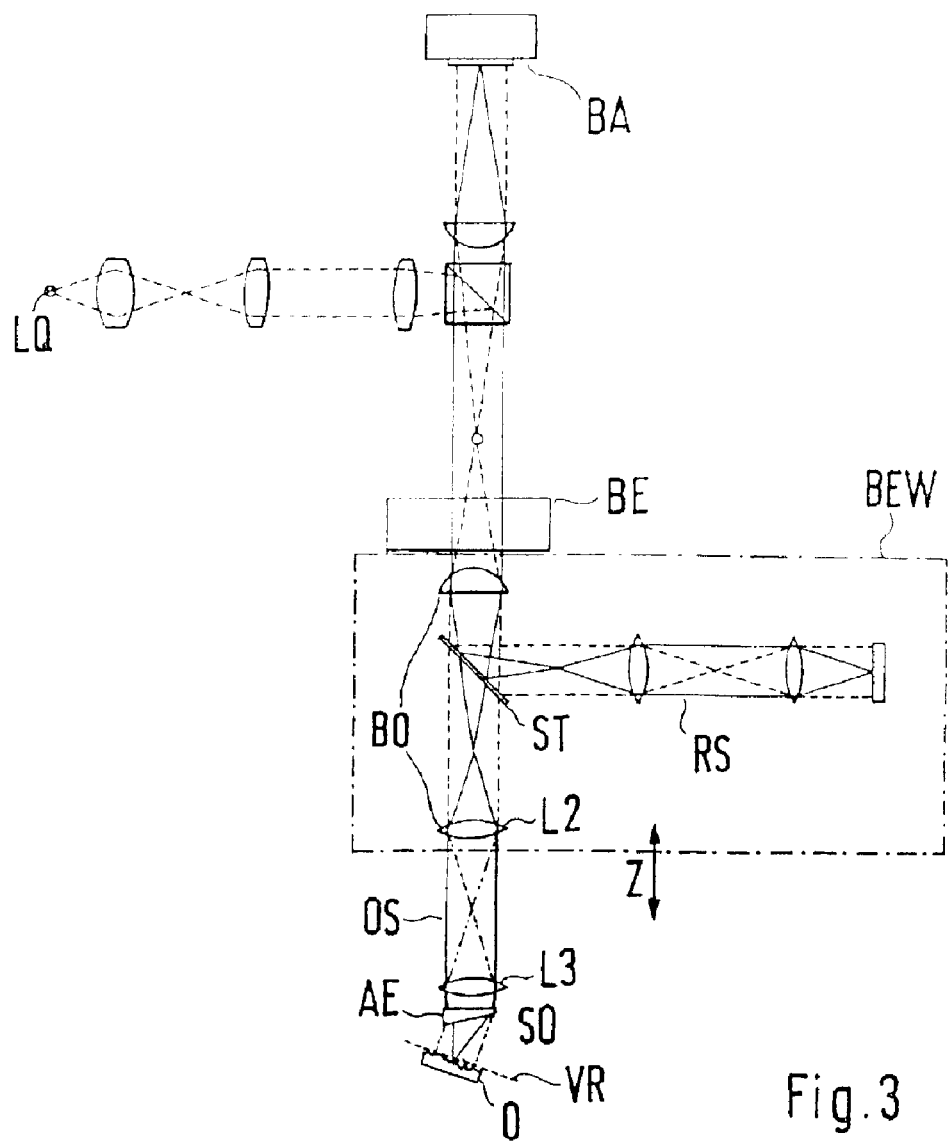
FIG. 3 shows another exemplary embodiment of the interferometric measuring device, with a different arrangement of the optically fixed elements in the object light path.

In another exemplary embodiment shown in FIG. 3, the fixed lens system SO includes an image-generating element, which changes the wave front and is in the form of the lens L3, and a deflecting unit in the form of a refracting element so that once again, an object surface disposed oblique in relation to the depth scanning direction is always measured in a positionally accurate manner. In this case, however, another element, which changes the wave front and is in the form of the lens L2, is disposed inside the moving unit BEW so that this embodiment does in fact also permit a simple adaptation in a scanning device, but on the other hand, the depth measurement range is limited to the depth of focus since the whole image plane does not move along with the depth scanning. The fixed lens system SO generates an image of the object toward infinity.

Figure 4:
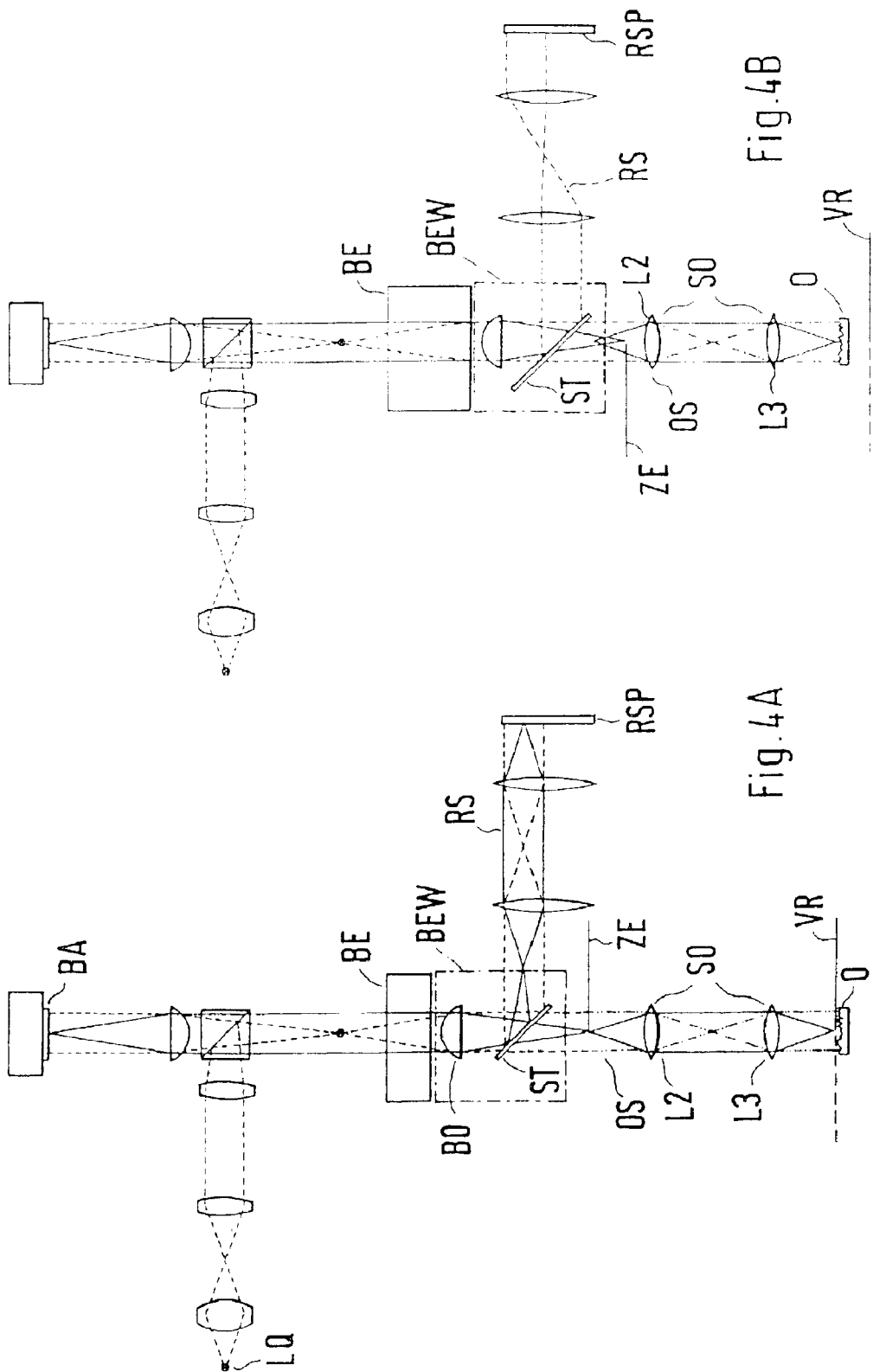
FIGS. 4A and 4B show another exemplary embodiment of the interferometric measuring device in which the size of a movable unit of the reference light path is shown in a reduced scale.

In the exemplary embodiment that is likewise shown in two different scanning positions in FIGS. 4A and 4B, the moving unit BEW is embodied so that it is very small; a greater diameter of image-generating lenses in the reference light path is used in connection with the beam distribution in the beam splitter ST.

Figure 5:
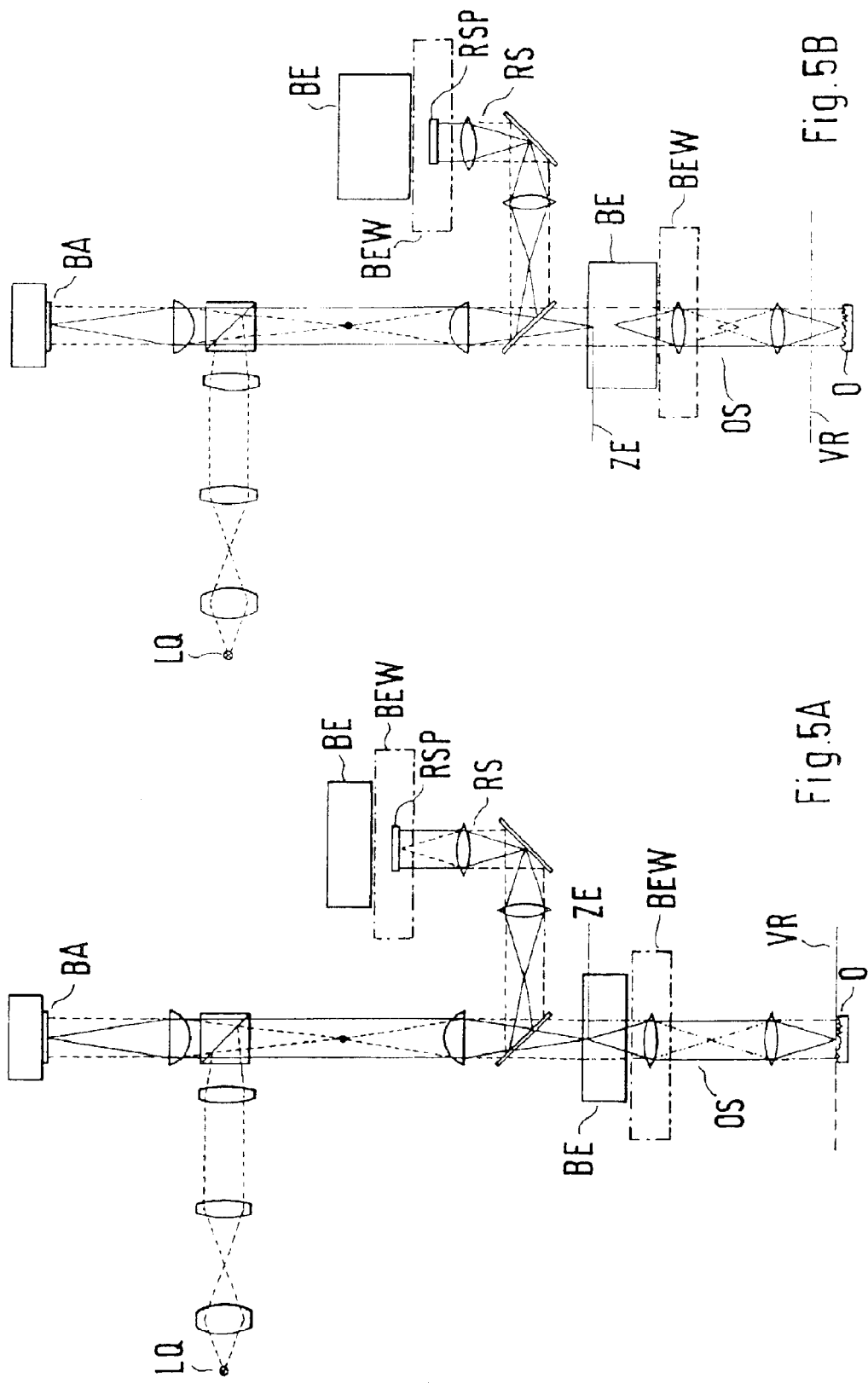
FIGS. 5A and 5B show another exemplary embodiment in which both the movable lens system and the reference mirror are moved.

In another exemplary embodiment shown in FIGS. 5A and 5B, a moving unit BEW is respectively provided in the reference light path and in the object light path, and is synchronously deflected by means of a respectively associated movement generator BE.

Other preferred exemplary embodiments are shown in FIGS. 6 to 10. In the exemplary embodiment according to FIG. 6, an intermediate image-generating device SO (also referred to below as the bayonet lens system) with intermediate image-generating lenses L2, L3, which is fixed in relation to the object O, is disposed as a fixed lens system SO in the object light path or object arm and generates a fixed intermediate image SZB of the object surface. The reference light path corresponds in length to the object light path so that a virtual reference VR is situated in the vicinity of the object surface. An image of the virtual reference VR is generated by the bayonet lens system SO as an image of the reference plane BR in the vicinity of the fixed intermediate image SZB. For a favorable design and operation, the bayonet lens system SO is embodied like an endoscope and is attached, for example, to a housing that contains the rest of the optical system. In another possible embodiment, the bayonet lens system SO is mechanically separate from the housing and is coupled to the object O in a stationary fashion.

The reference light path or reference arm contains optical elements, which essentially correspond to the optical elements of the object arm and are embodied in the form of a compensated lens system KSO so that interfering optical properties of the lens system in the object light path are compensated.

The fixed intermediate image SZB generated by the bayonet lens system SO is scanned in the depth direction, i.e. parallel to its normal, by means of the lens system BO, which can be moved parallel to the normal direction, i.e. along its optical axis (depth scanning). The image of the reference plane BR is situated in the depth of focus range of the movable objective, preferably in the object plane of the movable objective or the movable objective lens system. The depth scanning takes place by virtue of the fact that the movable objective lens system BO is moved relative to the fixed intermediate image SZB, which assures that the image of the reference plane BR moves synchronously along with the movable objective lens system BO.

As a result, during the scanning of the movable objective BO, the image of the reference plane BR is moved through the fixed intermediate image SZB.

The fixed intermediate image SZB is projected by the movable objective lens system BO directly or by means of at least one intermediate image generation step onto an image recorder BA, which has a multitude of image recording elements disposed next one another, e.g. a C.C.D camera, and is evaluated in a subsequent evaluation device E, in order to determine the surface shape, e.g. through detection of the maxima of the interference contrast, which forms the basis for the respective position of the movable objective BO.

In the image of the object on the image recorder BA, there is a higher interference contrast if a path difference between the object arm and the reference arm is less than the coherence length. Different intrinsically known methods can be used to obtain a 3-D vertical profile (see the references cited at the beginning).

Figure 6:
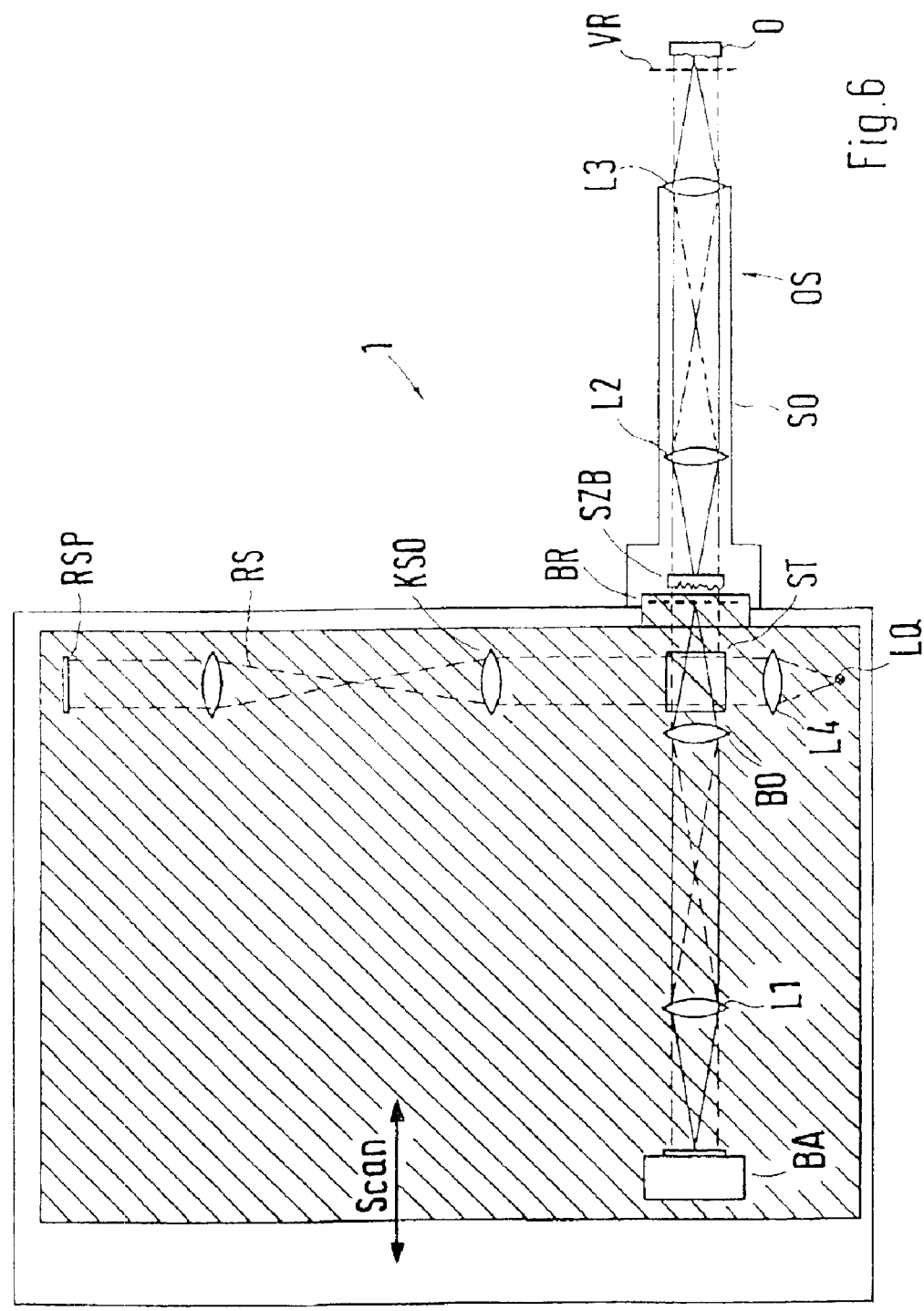
FIG. 6 is a schematic depiction of another exemplary embodiment of an interferometric measuring device.

For example, the design shown in FIG. 6 and also in the subsequent figures contains a Michelson interferometer. It is also possible to generate a number of intermediate images with the fixed bayonet lens system SO. The shaded region is moved for the scanning; this shaded region can be contained inside a housing, for example, against which in bayonet lens system SO is placed. Alternatively, the bayonet lens system SO can also be separate from the housing and can be connected to the object in a stationary fashion.

Figure 7:
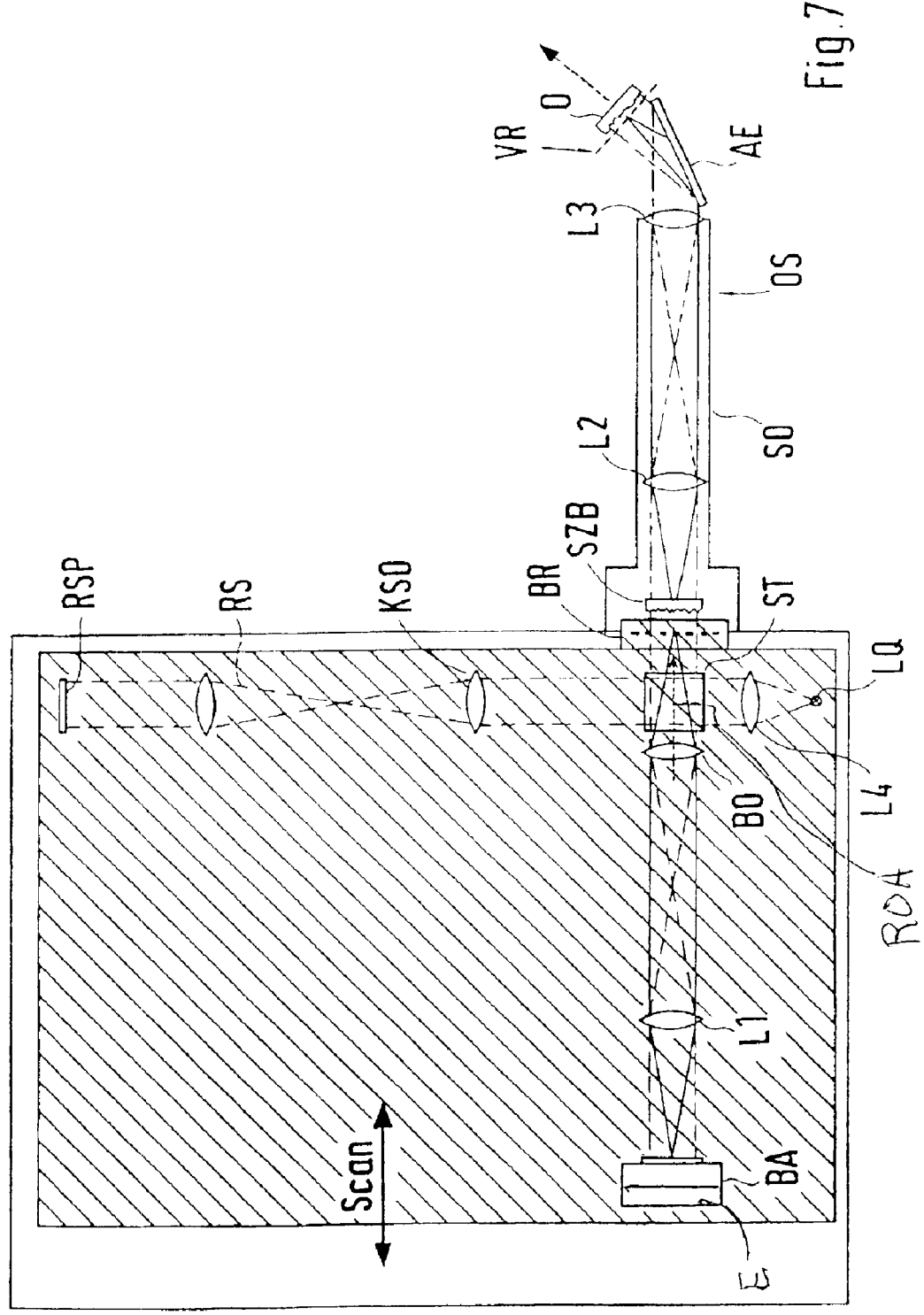
FIG. 7 shows the interferometric measuring device according to FIG. 6, with a device for measuring an oblique object surface.

In the design shown in FIG. 7, the surface of the object O to be measured is disposed oblique relative to the optical axis of the bayonet lens system SO and a deflecting element AE or a different image-generating unit is positioned in front of the object, which element generates a fixed intermediate image SZB that is aligned normally in relation to the optical axis ROA of the movable objective BO. The scanning of the fixed intermediate image SZB permits the scanning of the oblique object surface to be executed by means of simple measures since the viewing direction of the optical axis ROA of the movable objective BO is aligned at 0° in relation to the intermediate image. Then the scanning axis need only be aligned parallel to the axis of the movable objective BO. The viewing direction of the bayonet lens system SO is therefore independent of the scanning axis of the depth scanning.

Figure 8:
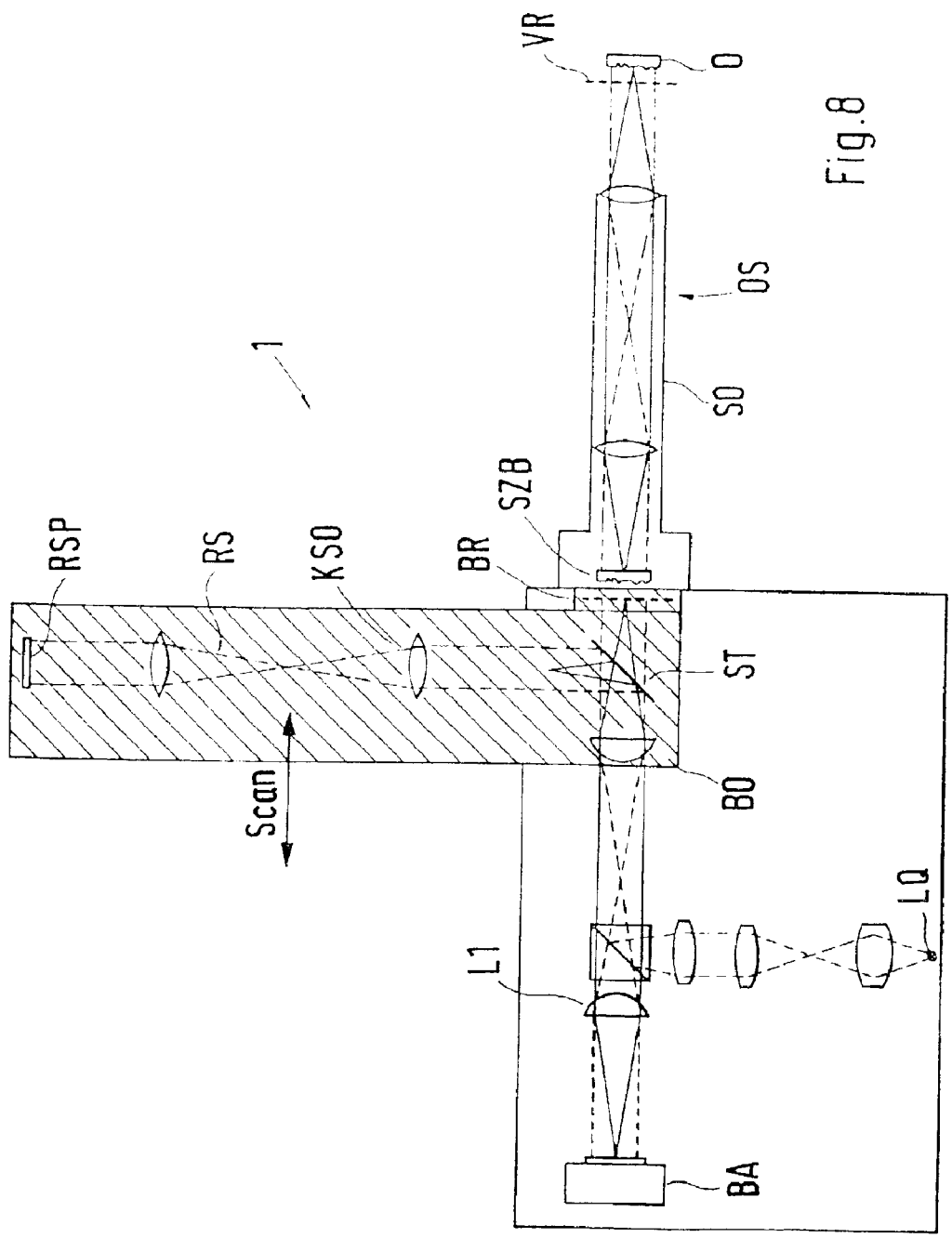
FIG. 8 shows another example of the interferometric measuring device in which the number of moving elements is reduced in comparison to FIGS. 6 and 7.

In the design of the interferometric measuring device 1 shown in FIG. 8, the number of moving components that execute the depth scanning is significantly reduced, as indicated by the number of elements depicted in the shaded region, which essentially includes the reference arm, the beam splitter ST, and the movable objective BO.

Figure 9:
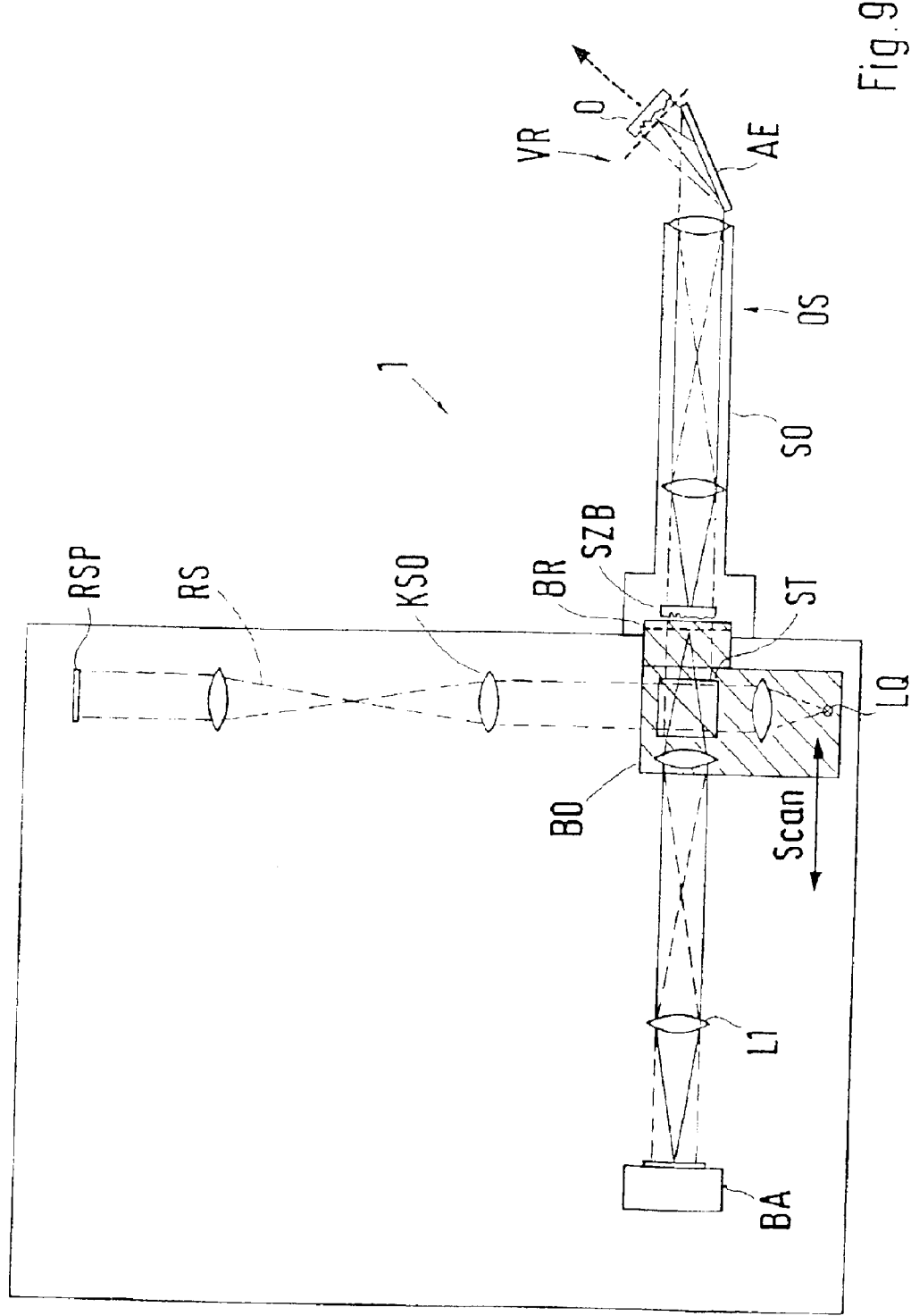
FIG. 9 shows another exemplary embodiment of the interferometric measuring device in which the number of moving elements is further reduced.

Another exemplary embodiment for the interferometric measuring device 1 with a scanning of the fixed intermediate image SZB is shown in FIG. 9. In this instance, in addition to the movable objective BO, the beam splitter ST and the illumination unit with the light source LQ are moved. A slight shifting of the reference beam lateral to the optical axis of the reference arm has practically no effect on the measuring result due to the relatively slight scanning movement distance.

Figure 10:
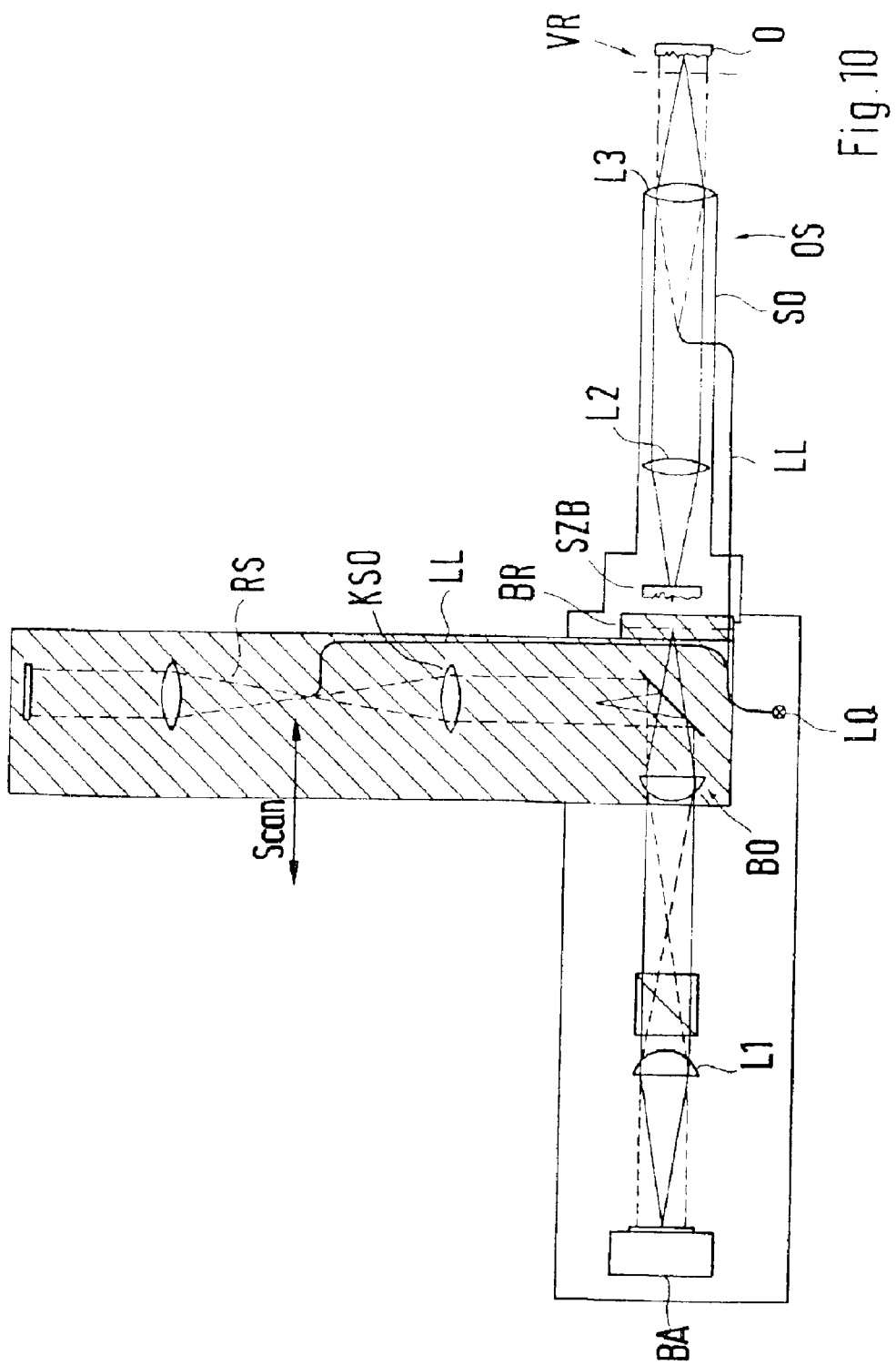
FIG. 10 shows another embodiment of the interferometric measuring device in which a fiber optic device is provided for illumination.

In the exemplary embodiment shown in FIG. 10, the object O is alternatively illuminated by means of a fiber optic light guide LL, which extends at least partially inside the bayonet lens system SO. This fiber optic illumination has the advantage of reducing reflections against the lenses of the bayonet lens system SO. In order to balance the optical path lengths and dispersion in the object arm and the reference arm, the fiber lengths and geometries in the two interferometer arms should be selected so as to correspond with each other to the greatest degree possible.

A variety of embodiments can be selected for the lenses contained in the interferometric measuring device, e.g. achromatic lenses, grin lenses (gradient index lenses), or rod-shaped lenses.

Figure 11:
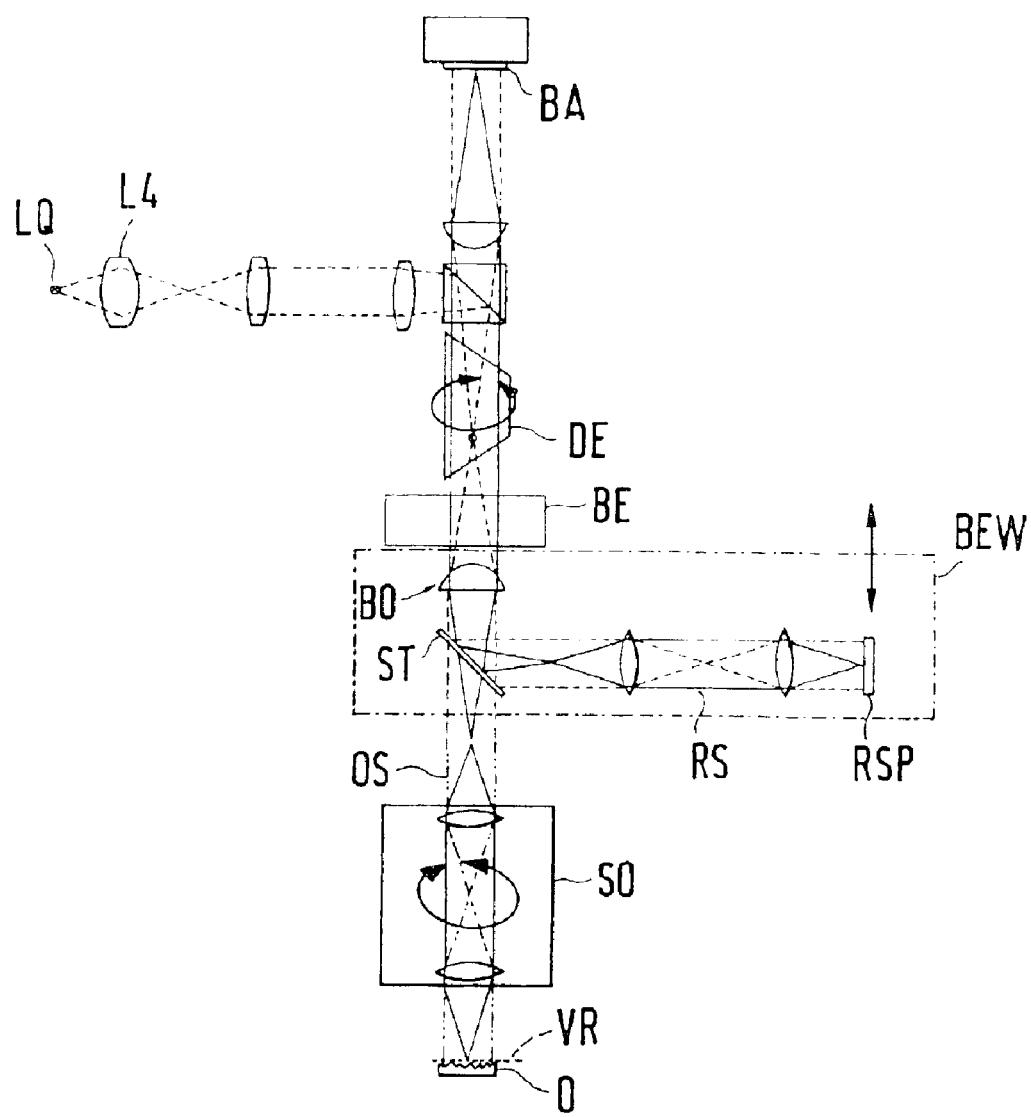
FIG. 11 shows another embodiment of the interferometric measuring device, with a device for rotating the image.

In the exemplary embodiment shown in FIG. 11, the image-generating lens system contains an optical element DE for rotating the image. If the fixed lens system SO is rotated in relation to the object, e.g. in order to measure different segments of a radially symmetrical object (e.g. a valve seat), then the image of the object O also rotates on the image recorder BA. However, it is advantageous to have a fixed image of the object on the image recorder BA. This can be achieved in that an optical element (e.g. a reversion prism, dove prism, etc.), which can compensate for the rotation of the image, is provided in the image-generating lens system, preferably outside the object light path.

Figure 12:
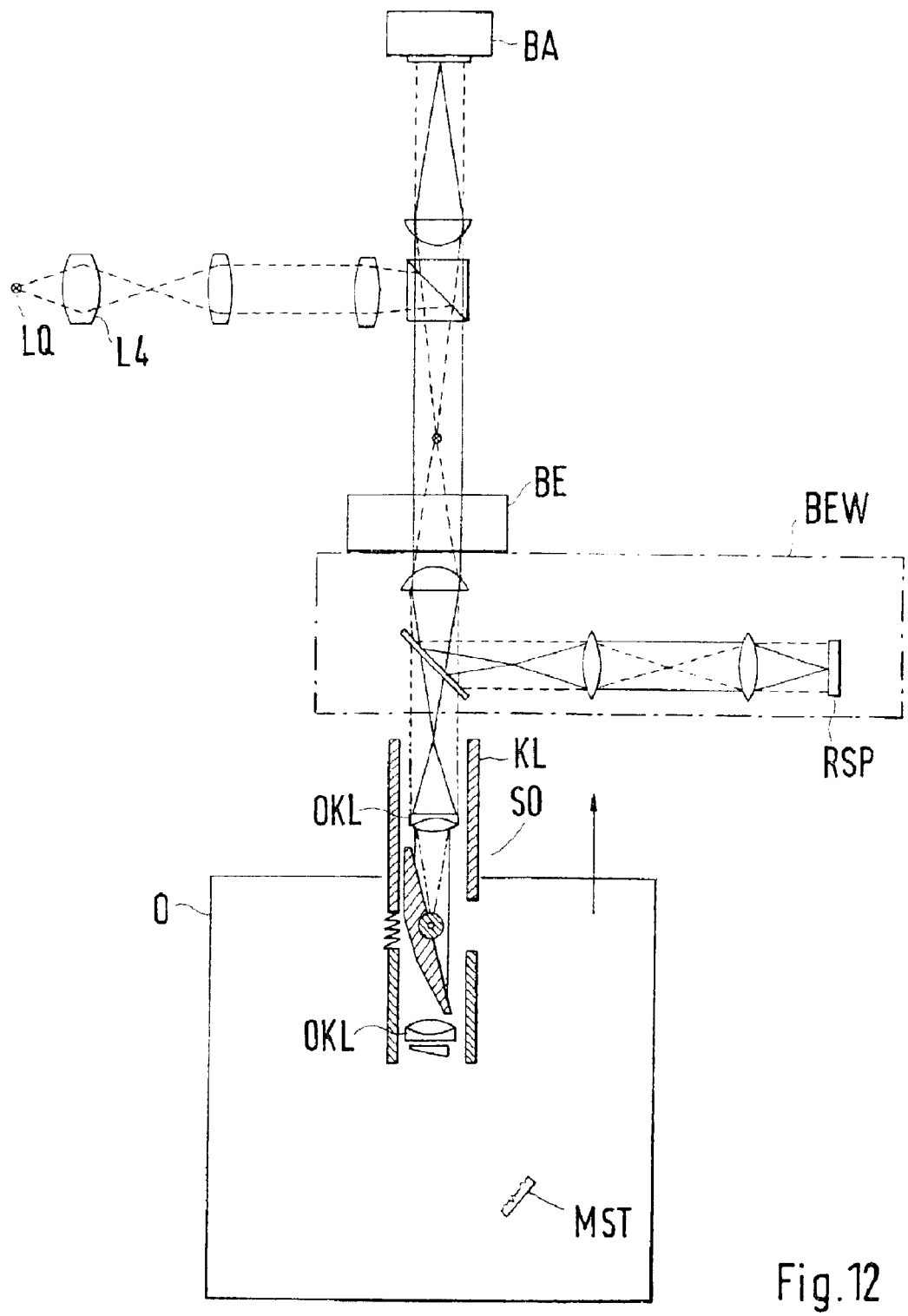
FIG. 12 shows an embodiment of the interferometric measuring device with a tilting endoscope, during an insertion procedure.
Figure 13:
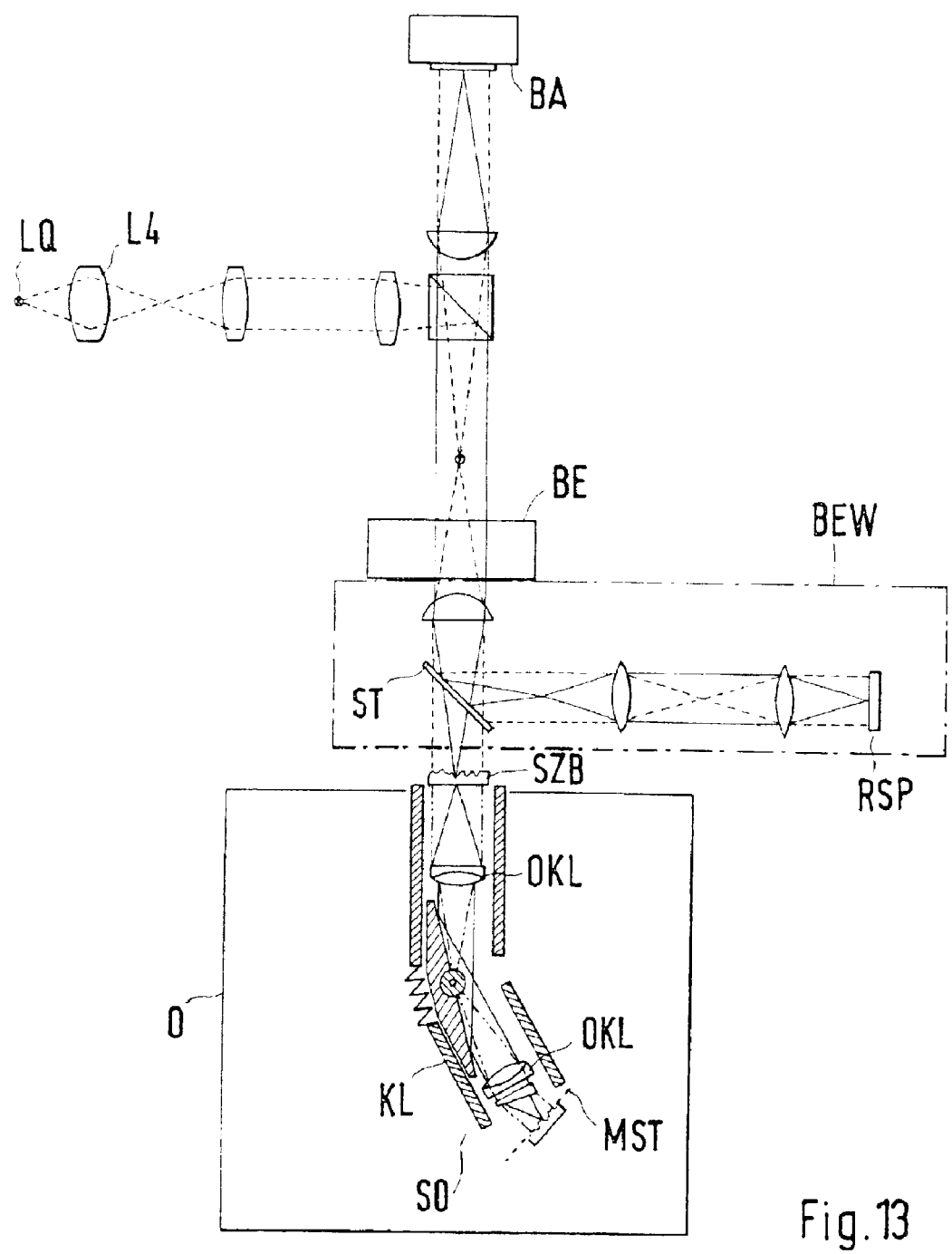
FIG. 13 shows the measuring device according to FIG. 12 in the measuring position, and FIGS. 14a) to c) show different depictions of the tilting endoscope.
Figure 14:
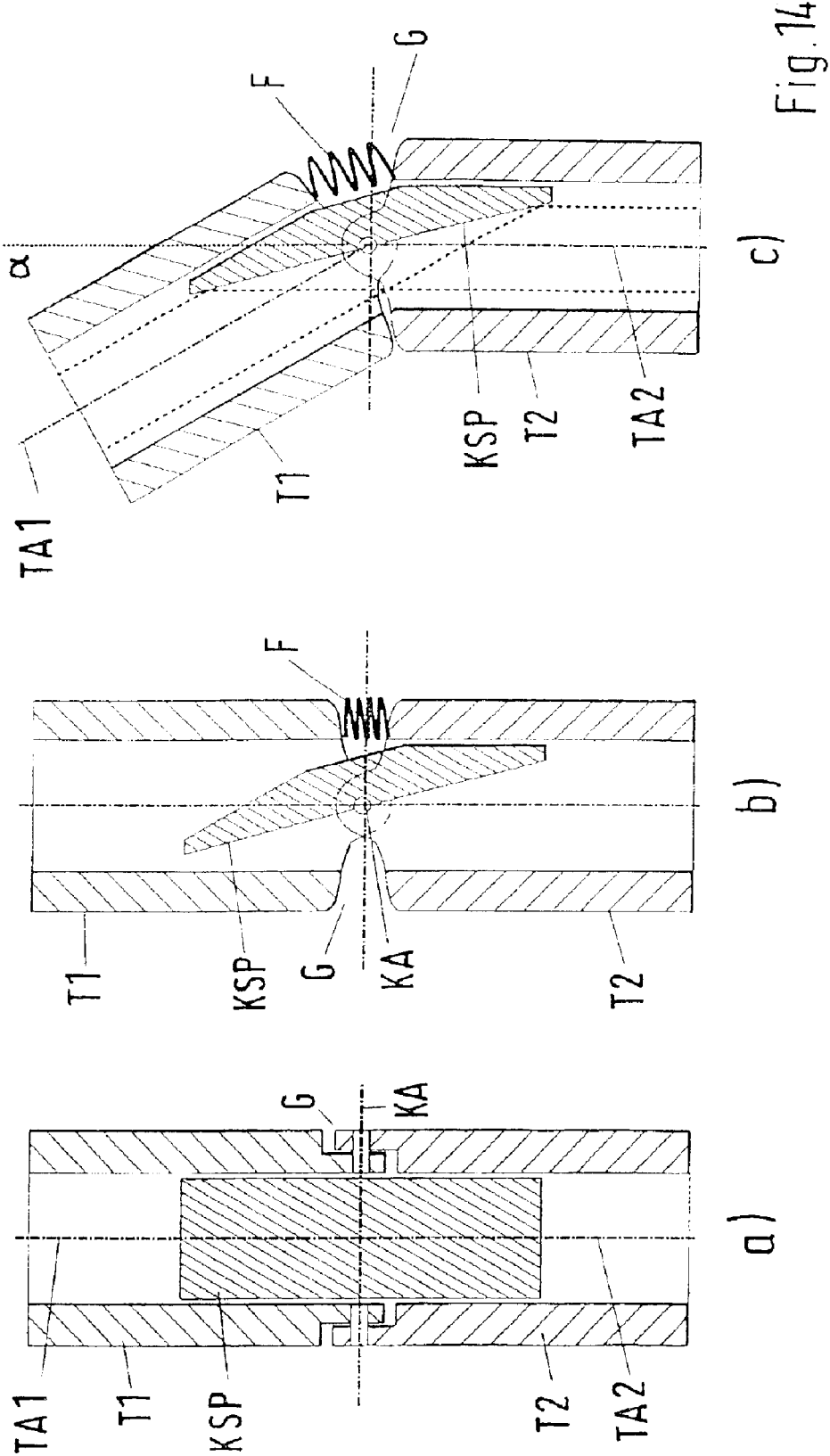

FIGS. 12 to 14 show another exemplary embodiment of the interferometric measuring device in which the fixed lens system SO is embodied as a tilting endoscope KL.

The tilting endoscope KL is comprised, for example, of two tubes T1, T2, which have respective tube axes TA1, TA2 and are connected to each other with a joint G in order to form a tilting axis KA of the one tube T1 in relation to the other tube T2. For example, the two tubes T1, T2 can assume two different tilt positions, which differ by a tilting angle α, as can be seen in FIGS. 14b) and c). In the current instance, the two tubes T1, T2 are mechanically produced so that in the untilted position, the two tube axes TA1, TA2 form an angle of 0°, whereas in the tilted position, they are oriented at the predetermined tilting angle α in relation to each other. Between the tubes T1, T2, which contain the optical components OKL of the tilting endoscope, a spring mechanism with a spring F is provided in the vicinity of the joint G. If the tilting endoscope KL is in the untilted position, then the spring F is under stress, whereas in the tilted position, the spring is unstressed. In the current instance, the endoscope lens system is designed for the tilted position. The endoscope lens system contains at least one optical deflecting element, e.g. a mirror KSP, which is disposed in the vicinity of the joint G. Prisms or gratings can also be conceivably used as deflecting elements, through which the optical axis is deflected in accordance with the tube axes TA1, TA2. As shown in FIG. 12, when inserted into the object O, the tilting endoscope KL is in the untilted position. If the spring is under stress, this insertion can be achieved by virtue of the endoscope having its own guide mechanism. However, the object itself can also serve as a guide mechanism, e.g. a guide bore in a valve seat measurement as shown in FIGS. 12 and 13. If the tilting endoscope KL is inserted completely into the object O or the component, then the joint G should be unconfined so that the tilting endoscope KL can assume the tilted position. The tilting endoscope KL is manufactured so that in the tilted position, it observes the measuring location MST precisely.

In the tilted position, the object surface to be observed is illuminated with a plane wave by the tilting endoscope KL and an image of it is generated directly or by means of an intermediate image on the image recorder BA (e.g. CCD camera). In the reference light path, the reference beam RS is reflected by the reference mirror RSP. In order to compensate the endoscope lens system, a lens system that is similar or corresponds to the endoscope lens system can also be placed here in the reference light path or reference arm. The data evaluation takes place as described in connection with the preceding exemplary embodiments.

The interferometer here can also be embodied other than as a Michelson interferometer (e.g. as a common path interferometer, a Mach-Zehnder interferometer, etc.).

What is claimed is:

1. An interferometric measuring device (1) for measuring the shape of a surface of an object (O) by means of white light interferometry, said interferometric measuring device (1) comprising
    a radiation source (LO) that emits short coherence radiation,
    a beam splitter (ST) arranged to cooperate with the radiation source (LQ) to produce an object beam (OS) and a reference beam (RS), said object beam (OS) being guided along an object light path to the object (O) and said reference beam (RS) being guided along a reference light path to a reflective reference plane (RSP),
    a fixed lens system (SO) arranged in the object light path and having a fixed relationship to the object (O),
    optical means for forming an intermediate image of the surface of the object, said optical means comprising said fixed lens system (SO),
    a movable lens system (BO) having an optical axis (ROA), wherein said movable lens system (BO) is followed in a direction of said optical axis (ROA) by said fixed lens system (SO) after reflection of said object beam (OS), and said movable lens system (BO) movable in said direction of said optical axis in order to perform a depth scan,
    an image recorder (BA) arranged to record radiation reflected by the object (O) and radiation reflected by the reflective reference plane (RSP) with image recording elements arranged next to each other on an extended planar surface thereof, said radiation reflected from the object and said radiation reflected from the reflective reference plane (RSP) being arranged to interfere with each other, said image recording elements consisting of pixels, and
    an evaluation device (E) connected to the image recorder (BA) to determine the surface shape from the interfering radiation received by the image recorder.

2. The measuring device as defined in claim 1, wherein the fixed lens system (SO) has elements that deform an incident wave front.

3. The measuring device as defined in claim 1, wherein said fixed lens system (SO) is at least partially embodied as an endoscope.

4. The measuring device as defined in claim 1, wherein said fixed lens system (SO) generates an image of the object at infinity.

5. The measuring device as defined in claim 1, wherein said movable lens system (BO) is arranged entirely outside, partially inside and outside or entirely inside the object light path.

6. The measuring device as defined in claim 1, wherein said movable lens system (BO) includes movable optical elements supported so as to be movable on the optical axis.

7. The measuring device as defined in claim 1, wherein said fixed lens system (SO) forms an image of a virtual reference plane (VR) at a depth in a focus range of an image-generating lens system.

8. The measuring device as defined in claim 7, wherein the image of the virtual reference plane (VR) is situated in an image plane of the image-generating lens system.

9. The measuring device as defined in claim 7 or 8, wherein the image of the reference plane (VR) moves synchronously with the image plane of the image-generating lens system when the movable lens system (BO) is moved.

10. The measuring device as defined in claim 1, wherein the fixed lens system (SO) is embodied as a fixed intermediate image-generating device (L2, L3) which generates an intermediate image (SZB) of the object surface that is fixed in relation to the object (O), and that the movable lens system (BO) is embodied as an objective lens system, which is disposed behind the fixed intermediate image (SZB) in the object light path and is movable in the direction of said optical axis (ROA), in order to scan the fixed intermediate image (SZB), which is aligned normal to said optical axis, in a depth direction (Z) and to generate an image of the fixed intermediate image on the image recorder (BA) directly or by means of one or more intermediate image-generating means.

11. The measuring device as defined in claim 10, wherein the fixed intermediate image-generating device (L2, L3) has an identical image-generating scale for all object points appearing on the fixed intermediate image (SZB).

12. The measuring device as defined in claim 11, wherein the fixed intermediate image-generating device (L2, L3) is embodied as a telecentric image-generating device arranged in a 4f apparatus.

13. The measuring device as defined in claim 10, wherein respective position of the movable lens system (BO) at which interference contrast is greatest is detected for each of said pixels.

14. The measuring device as defined in claim 10, wherein, if a viewing direction of the fixed intermediate image-generating device (L2, L3) diverges from a normal to the object surface, a deflecting element (AE) is provided in the object light path for generating the fixed intermediate image (SZB).

15. The measuring device as defined in claim 10, further comprising a movable unit, said movable unit including an illumination unit with the light source (LQ), the beam splitter (ST) and the movable lens system (BO) or said movable unit including only the beam splitter (ST) in addition to the movable lens system (BO).

16. The measuring device as defined in claim 10, wherein the fixed intermediate image-generating device (L2, L3) is embodied as an endoscope.

17. The measuring device as defined in claim 1, further comprising a set of fiber optics (LL) provided for illumination of the object (O) and the reference reflective plane (RSP).

18. The measuring device as defined in claim 1, wherein said movable lens systems (BO) and said fixed lens System (SO) each include at least one of individual lenses, gradient index lenses, rod-shaped lenses, diffractive elements, prisms and combinations thereof.

19. An interferometric measuring device (1) for measuring the shape of a surface of an object (O) by means of white light interferometry, said interferometric measuring device (1) comprising a radiation source (LQ) that emits short coherence radiation, a beam splitter (ST) arranged to cooperate with the radiation source (LQ) to produce an object beam (OS) and a reference beam (RS), said object beam (OS) being guided along an object light path to the object (O) and said reference beam (RS) being guided along a reference light path to a reflective reference plane (RSP), an image recorded (BA) arranged to record radiation reflected by the object (O) and radiation reflected by the reflective reference plane (RSP) with image recording elements disposed over an extended surface area thereof, said radiation reflected from the object and said radiation reflected from the reflective reference plane (RSP) being arranged to interfere with each other, an evaluation device (E) connected to the image recorder to determine the surface shape from the interfering radiation received by the image recorder, and an image-generating lens system for forming an image on the image recording elements of the image recorder, said image-generating lens system including a fixed lens system (SO) arranged in the object light path and having a fixed relationship to the object (O), a movable lens system (BO) having an optical axis (ROA) and following said fixed lens system (SO), said movable lens system (BO) being movable in a direction of said optical axis, and an optical image-rotating element (DE) arranged in or out of the object light path, wherein said optical image-rotating element comprises means for rotating the image formed on the image recording elements in order to facilitate evaluation.

20. An interferometric measuring device (1) for measuring the shape of a surface of an object (O) by means of white light interferometry, said interferometric measuring device (1) comprising a radiation source (LQ) that emits short coherence radiation, a beam splitter (ST) arranged to cooperate with the radiation source (LQ) to produce an object beam (OS) and a reference beam (RS), said object beam (OS) being guided alone an object light path to the object (O) and said reference beam (RS) being guided along a reference light path to a reflective reference plane (RSP), a fixed lens system (SO) arranged in the object light path and having a fixed relationship to the object (O), a movable lens system (BO) having an optical axis (ROA) and following said fixed lens system (SO), which is movable in a direction of said a optical axis, an image recorder (BA) arranged to record radiation reflected by the object (O) and radiation reflected by the reflective reference plane (RSP) with image recording elements disposed over an extended surface area thereof, said radiation reflected from the object and said radiation reflected from the reflective reference plane RSP being arranged to interfere with each other, and an evaluation device (E) connected to the image recorder to determine the surface shape from the interfering radiation received by the image recorder; wherein the fixed lens system (SO) comprises a tilting endoscope (KL) arranged in the object light path and said tilting endoscope has at least two tilt positions with an angle ($\alpha$) between an untilted position and a tilted position.

21. The measuring device as defined in claim 20, wherein the tilting endoscope (KL) has two tubes (T1, T2), which are connected to each other by means of a joint (G) and which contain optical components (OKL) of the tilting endoscope (KL) including a deflecting element (KSP).

22. The measuring device as defined in claim 21, wherein a spring mechanism (F) is provided in the two tubes in the vicinity of the joint (G) and cooperates with the two tubes (T1, T2).

23. An interferometric measuring device (1) for measuring the shape of a surface of an object (O) by means of white light interferometry, said interferometric measuring device (1) comprising a radiation source (LQ) that emits short coherence radiation;

a beam splitter (ST) arranged to cooperate with the radiation source (LQ) to produce an object beam (OS) and a reference beam (RS), said object beam (OS) being guided along an object light path to the object (O) and said reference beam (RS) being guided along a reference light path to a reflective reference plane (RSP);

an image recorder (BA) arranged to record radiation reflected by the object (O) and radiation reflected by the reflective reference plane (RSP) with pixels arranged next to each other on an extended planar surface, wherein said object (O) and said reflective reference plane (RSP) are arranged so that said radiation reflected from the object and said radiation reflected from the reflective reference plane (RSP) interfere with each other;

an image-generating lens system for generating an image of the object on the image recorder, wherein said image-generating lens system comprises a movable lens system (BO) having an optical axis (ROA) and a fixed lens system (SO) following said movable lens system (BO) in a direction of said optical axis in order to perform a depth scan, said movable lens system (BO) is movable in said direction of said optical axis and said fixed lens system (SO) is at least part of a means for forming a fixed intermediate image (SZB) of said surface of said object, which is scanned by said movable lens system (BO); and an evaluation device (E) connected to the image recorder (BA) to determine said shape of said surface of said object from said interfering radiation received by said pixels of said image recorder.

24. An interferometric measuring device (1) for measuring the shape of a surface of an object (O) by means of white light interferometry, said interferometric measuring device (1) comprising a radiation source (LQ) that emits short coherence radiation, a beam splitter (ST) arranged to cooperate with the radiation source (LQ) to produce an object beam (OS) and a reference beam (RS), said object beam (OS) being guided along an object light path to the object (O) and said reference beam (RS) being guided along a reference light path to a reflective reference plane (RSP), a fixed lens system (SO) arranged in the object light path and having a fixed relationship to the object (O), a movable lens system (BO) having an a optical axis (ROA) and following said fixed lens system (SO), which is movable in a direction of said optical axis, an image recorder (BA) arranged to record radiation reflected by the object (O) and radiation reflected by the reflective reference plane (RSP) with image recording elements disposed over an extended surface area thereof, said radiation reflected from the object and said radiation reflected from the reflective reference lane (RSP) being arranged to interfere with each other, and an evaluation device (E) connected to the image recorder to determine the surface shape from the interfering radiation received by the image recorder;

wherein the fixed lens system (SO) is embodied as a fixed intermediate image-generating device (L2, L3) which generates an intermediate image (SZB) of the object surface that is fixed in relation to the object (O), and that the movable lens system (BO) is embodied as an objective lens system, which is disposed behind the fixed intermediate image (SZB) in the object light path and is movable in the direction of said optical axis (ROA), in order to scan the fixed intermediate image (SZB), which is aligned normal to said optical axis, in a depth direction (Z) and to generate an image of the fixed intermediate image on the image recorder (BA) directly or by means of one or more intermediate image-generating means;

wherein a compensating lens system (KSO), which at least partially compensates the fixed lens system or the movable lens system in the object light path, is arranged in the reference light path for optical compensation.

* * * * *